(12) United States Patent
Zheng et al.

(10) Patent No.: US 12,092,714 B2
(45) Date of Patent: Sep. 17, 2024

(54) SHIMMING METHOD AND DEVICE, ELECTRONIC DEVICE, AND STORAGE MEDIUM

(71) Applicant: SHENZHEN INSTITUTES OF ADVANCED TECHNOLOGY CHINESE ACADEMY OF SCIENCES, Shenzhen (CN)

(72) Inventors: Hairong Zheng, Shenzhen (CN); Qiaoyan Chen, Shenzhen (CN); Ye Li, Shenzhen (CN); Chao Luo, Shenzhen (CN); Xin Liu, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 93 days.

(21) Appl. No.: 17/992,868

(22) Filed: Nov. 22, 2022

(65) Prior Publication Data

US 2023/0152400 A1    May 18, 2023

Related U.S. Application Data

(63) Continuation of application No. PCT/CN2021/138523, filed on Dec. 15, 2021.

(30) Foreign Application Priority Data

Nov. 16, 2021   (CN) .......................... 202111357763.8

(51) Int. Cl.
*G01R 33/3875* (2006.01)
*A61B 5/055* (2006.01)

(52) U.S. Cl.
CPC .......... *G01R 33/3875* (2013.01); *A61B 5/055* (2013.01)

(58) Field of Classification Search
CPC .............. G01R 33/387; G01R 33/3875; G01R 33/56536; G01R 33/3802; A61B 5/055; A61B 2503/40; A61B 5/0042
See application file for complete search history.

(56) References Cited

U.S. PATENT DOCUMENTS

2006/0197526 A1    9/2006  Weiger et al.
2016/0274202 A1*   9/2016  Stemmer .......... G01R 33/56563
(Continued)

FOREIGN PATENT DOCUMENTS

CN   102879753 A    1/2013
CN   104573308 A    4/2015
(Continued)

OTHER PUBLICATIONS

Du, Jun-Jie, et al. "A novel design methodology for active shim coil." Measurement Science and Technology 23.8 (2012): 085502. (Year: 2012).*

*Primary Examiner* — Rishi R Patel

(57) ABSTRACT

A shimming method and device, an electronic device, and a storage medium are disclosed. The shimming method includes: obtaining object static magnetic field distribution information corresponding to a target object, the object static magnetic field distribution information including the static magnetic field distribution information of the target object under the action of a main magnet of a magnetic resonance system; determining a target static magnetic field based on the object static magnetic field distribution information and a preset shim coil magnetic field distribution model; and adjusting at least one shim coil parameter in the shim coil magnetic field distribution model until a magnetic field uniformity of the target static magnetic field satisfies a preset condition, and accordingly obtaining at least one target shim coil parameter.

12 Claims, 3 Drawing Sheets

(56) References Cited

U.S. PATENT DOCUMENTS

2016/0274205 A1* 9/2016 Stemmer .............. G01R 33/543
2019/0246939 A1* 8/2019 Abe ....................... H01F 41/02

FOREIGN PATENT DOCUMENTS

| CN | 105044636 A | 11/2015 |
| CN | 106990373 A | 7/2017 |
| CN | 108387857 A | 8/2018 |
| CN | 110632541 A | 12/2019 |
| CN | 110927642 A | 3/2020 |
| CN | 111175336 A | 5/2020 |
| CN | 113325351 A | 8/2021 |
| EP | 1662270 A1 | 5/2006 |
| WO | 2015173921 A1 | 11/2015 |
| WO | 2021109847 A1 | 6/2021 |

* cited by examiner

S101

Obtaining object static magnetic field distribution information corresponding to a target object, wherein the object static magnetic field distribution information comprises static magnetic field distribution information of the target object under the action of a main magnet of a magnetic resonance system

S102

Determining a target static magnetic field based on the object static magnetic field distribution information and a preset shim coil magnetic field distribution model

S103

Adjusting at least one shim coil parameter in the preset shim coil magnetic field distribution model until a magnetic field uniformity of the target static magnetic field satisfies a preset condition, and accordingly obtaining at least one target shim coil parameter

FIG. 1

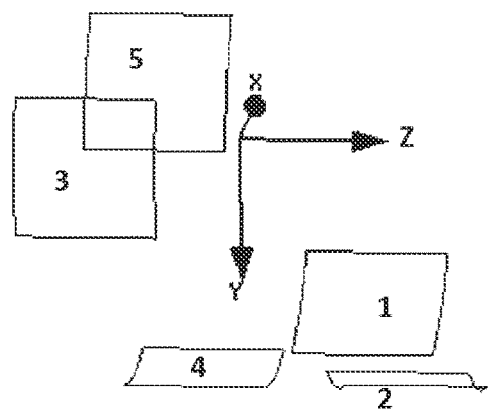

FIG. 2

SHIMMING METHOD AND DEVICE, ELECTRONIC DEVICE, AND STORAGE MEDIUM

CROSS-REFERENCE TO RELATED APPLICATIONS

This application claims the priority and benefit of Chinese patent application 202111357763.8, entitled "Shimming Method and Device, Electronic Device, and Storage Medium" and filed Nov. 16, 2021, with China National Intellectual Property Administration, the entire contents of which are incorporated herein by reference.

TECHNICAL FIELD

This application relates to the field of electromagnetic technology, and more particularly relates to a shimming method and device, an electronic device, and a storage medium.

BACKGROUND

When an organism is imaged by a magnetic resonance system, due to the difference in magnetic susceptibility between different tissues of the organism, a local non-uniform or inhomogeneous magnetic field is produced at the junction of the tissues, resulting in image artifacts in the acquired image. Often, the non-uniformity or inhomogeneity of the magnetic field can be reduced by adding additional shim coils to the magnetic resonance system thereby improving image quality.

However, the performance of the current shim coils is not optimized enough, which leads to the problem of uneven or inhomogeneous magnetic field distribution not to be well resolved.

SUMMARY

In view of the above, embodiments of the present application provide a shimming method and device, an electronic device, and a storage medium, so as to solve the problem of uneven distribution of the magnetic field in the organism imaged in the magnetic resonance system of the related art.

According to a first aspect of the embodiments of the present application, there is provided a shimming method, including:
  obtaining object static magnetic field distribution information corresponding to a target object, where the object static magnetic field distribution information is the static magnetic field distribution information of the target object under the action of a main magnet of a magnetic resonance system;
  determining the target static magnetic field based on the object static magnetic field distribution information and a preset shim coil magnetic field distribution model; and
  adjusting at least one shim coil parameter in the shim coil magnetic field distribution model until the magnetic field uniformity of the target static magnetic field satisfies a preset condition, and accordingly obtaining at least one target shirrs coil parameter.

In some embodiments, the at least one shim coil parameter includes any one or more selected from the group consisting of: a number of channels, a size, a spatial position, a current magnitude, and a number of turn of the at least one shim coil.

In some embodiments, before obtaining the object static magnetic field distribution information corresponding to the target object, the shimming method further includes:
  according to Biot-Savart law, determining the magnetic field distribution information of the shim coil magnetic field distribution model.

In some embodiments, obtaining the object static magnetic field distribution information corresponding to the target object includes:
  obtaining the object static magnetic field distribution information corresponding to each of a number of n target objects, n being a positive integer greater than 1; and accordingly, determining the target static magnetic field based on the object static magnetic field distribution information and the preset shim coil magnetic field distribution model includes:
  determining the target static magnetic field based on the object static magnetic field distribution information corresponding to each of the n target objects and the preset shim coil magnetic field distribution model.

In some embodiments, the shim coil magnetic field distribution model includes shim coil units of a number of in channels, n being a positive integer greater than 1. Accordingly, determining the target static magnetic field based on the object static magnetic field distribution information corresponding to each of the n target objects and the preset shim coil magnetic field distribution model includes:
  determining the target static magnetic field using the objective function $$F = \sum_{i=1}^{n}\sum_{j=1}^{m}(C_j b_j + B_i);$$

where F denotes the magnetic field distribution information of the target static magnetic field, $C_j$ denotes a current magnitude of the shim coil unit of the j-th channel in the shim coil magnetic field distribution model, and $b_j$ denotes the magnetic field distribution information of the shim coil unit of the j-th channel in the shim coil magnetic field distribution model, and $B_i$ denotes the object static magnetic field distribution information of the i-th target object.

In some embodiments, adjusting the at least one shim coil parameter in the shim coil magnetic field distribution model until the magnetic field uniformity of the target static magnetic field satisfies the preset condition so as to obtain the at least one target shim coil parameter includes:
  according to a particle swarm algorithm and the objective function, adjusting at least one shim coil parameter in the shim coil magnetic field distribution model until a standard deviation of the magnetic field distribution of the target static magnetic field is less than a preset threshold or until the number of iterations of the particle swarm algorithm reaches a preset number, so as to obtain the at least one target shim coil parameter.

In some embodiments, adjusting the at least one shim coil parameter in the shim coil magnetic field distribution model according to the particle swarm algorithm and the objective function until the standard deviation of the magnetic field distribution of the target static magnetic field is less than the preset threshold or until the number of iterations of the particle swarm algorithm reaches the preset number so as to obtain the at least one target shim coil parameter includes:
  for each shim coil magnetic field distribution model with a different number of channels, adjusting at least one sub-shim coil parameter in the shim coil magnetic field distribution model according to the particle swarm algorithm and the objective function, until the number of iterations of the particle swarm algorithm reaches the preset number of times to obtain at least one sub-target shim coil parameter corresponding to each of the shim coil magnetic field distribution models;

according to the respective at least one sub-target shim coil parameter corresponding to each of the shim coil magnetic field distribution models and the objective function, determining the standard deviation of the magnetic field distribution of the target static magnetic field corresponding to each of the shim coil magnetic field distribution models; and taking the shim coil magnetic field distribution model with the minimum standard deviation of the magnetic field distribution of the target static magnetic field as the target shim coil magnetic field distribution model; and using the number of channels and the at least one sub-target shim coil parameter of the target shim coil magnetic field distribution model as the at least one target shim coil parameter.

According to a second aspect of the embodiments of the present application, there is provided a shimming device, including:

an object static magnetic field distribution information acquisition unit configured to obtain object static magnetic field distribution information corresponding to a target object, where the object static magnetic field distribution information is the static magnetic field distribution information of the target object under the action of a main magnet of a magnetic resonance system;

a target static magnetic field determination unit configured to determine a target static magnetic field based on the object static magnetic field distribution information and a preset shim coil magnetic field distribution model; and a target shim coil parameter determination unit configured to adjust at least one shim coil parameter in the shim coil magnetic field distribution model until the magnetic field uniformity of the target static magnetic field satisfies a preset condition, and accordingly Obtaining at least one target shim coil parameter.

According to a third aspect of the embodiments of the present application, there is provided an electronic device, which includes a memory, a processor, and a computer program that is stored in the memory and that is executable on the processor. When the processor executes the computer program, the electronic device is caused to perform the operations of the shimming methods disclosed herein.

According to a fourth aspect of the embodiments of the present application, there is provided a computer-readable storage medium in which a computer program is stored. When the computer program is executed by the processor, the electronic device is caused to perform the operations of the shimming methods disclosed herein.

According to a fifth aspect of the embodiments of the present application, there is provided a computer program product. When the computer program product is executed on an electronic device, the electronic device is caused to perform the shimming method according to any one solution disclosed in the above first aspect.

Embodiments of the present application may provide the following benefits compared with the related art. In the embodiments of the present application, the static magnetic field distribution information of a target object under the action of a main magnet of a magnetic resonance system, namely the object static magnetic field distribution information, is obtained, and then according to the object static magnetic field distribution information and a preset shim coil magnetic field distribution model, a target static magnetic field is determined. Then, at least one shim coil parameter in the shim coil distribution model is adjusted in order that the magnetic field uniformity of the target static magnetic field satisfies a preset condition, and accordingly at least one target shim coil parameter is obtained. Since the target static magnetic field is determined based on the object static magnetic field distribution information of the target object and the preset shim coil magnetic field distribution model, the target static magnetic field can represent the static magnetic field of the magnetic resonance system when the magnetic resonance system is in an operating state in which at least one shim coil is superposed and the target object is present. By adjusting the shim coil parameters until the magnetic field uniformity of the target static magnetic field satisfies the preset condition, the target shim coil parameters that are able to satisfy the shimming effect can be obtained, so that the magnetic resonance system can ensure the uniformity of the static magnetic field distribution during operation based on the target shim coil parameters, thereby improving the magnetic resonance imaging effect.

BRIEF DESCRIPTION OF DRAWINGS

For a better understanding of the technical solutions provided in the embodiments of the present application, hereinafter the accompanying drawings that are required to be used in the description of the embodiments or the related art will be briefly described.

FIG. 1 is a flowchart of a shimming method according to an embodiment of the present application.

FIG. 2 is a schematic diagram of a shim coil according to an embodiment of the present application.

DETAILED DESCRIPTION OF EMBODIMENTS

Figure 3:
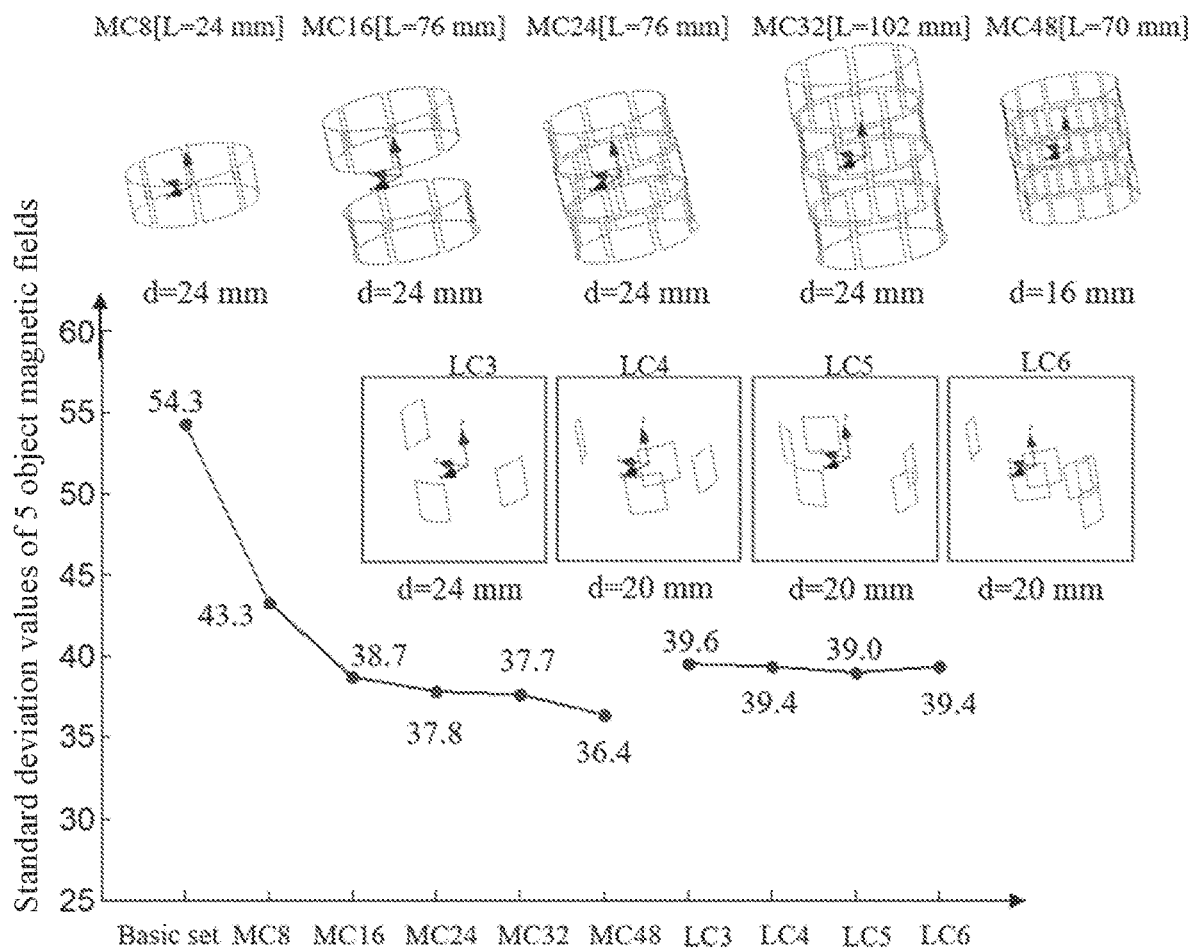
FIG. 3 is a schematic diagram showing the comparison of simulated shimming results of the performance of shim coils with different structures according to an embodiment of the present application.

Hereinafter, for purposes of illustration rather than limitation, specific details, such as specific system structures and technologies, are provided for a thorough understanding of the embodiments of the present application. However, it will be apparent to those having ordinary skill in the art that the present application may be practiced by other embodiments without these specific details. In other instances, detailed descriptions of well-known systems, devices, circuits, and methods are omitted so as not to obscure the description of the present application with unnecessary detail.

As used in this specification and the appended claims, the term "comprising" or "including" indicates the presence of the described feature(s), integer(s), step(s), operation(s), element(s), and/or component(s), but does not necessarily exclude the presence or addition of one or more other features, integers, steps, operations, elements, components, and/or sets thereof.

In order to illustrate the technical solutions described in the present application, the following specific embodiments are used for description.

In a magnetic resonance system, the non-uniformity or inhomogeneity of the static magnetic field may be reduced by adding one or more shim coils thereby improving the magnetic resonance imaging effect of the magnetic resonance system. However, the performance of the shim coil(s) actually added in the magnetic resonance system may not be optimal, which leads to the uniformity problem of the magnetic field distribution in the magnetic resonance system after adding the shim coil(s).

In order to solve this technical problem, embodiments of the present application provide a shimming method and device, an electronic device, and a storage medium. Based on the object static magnetic field distribution information of the target object as well as the preset shim coil magnetic field distribution model, the static magnetic field (i.e., the target static magnetic field) that is able to indicate that the magnetic resonance system is in an operating state in which at least one shim coil is superposed and an object to be imaged is present in the magnetic resonance system is obtained. Then, by adjusting the shim coil parameters until the magnetic field uniformity of the target static magnetic field satisfies the preset condition, the target shim coil parameters that are able to satisfy the shimming effect can be obtained, which enable the magnetic resonance system to ensure the uniformity of the static magnetic field distribution during operation based on the target shim coil parameters, thereby improving the magnetic resonance imaging effect.

In a magnetic resonance system, shim coils may include three types: spherical harmonic function shim coils, multi-shim coils, and local shim coils. Among them, the spherical harmonic function shim coil may need to increase the order to achieve a desired shimming effect. However, increasing the order of the spherical harmonic shim coil may bring some other practical problems, such as the reduction of utilization of the effective space, the deterioration of the coil efficiency, the need to additionally consider a cooling system for the shim coil, the need to increase the number of power amplifiers, etc. That is, the spherical harmonic function shim coil has certain defects. Compared with the spherical harmonic function shim coil, the multi-shim coil can generate a relatively complex high-order magnetic field through multiple simple coil loops to obtain a desired shimming capability. However, it may reduce the signal-to-noise ratio of magnetic resonance imaging, and will have a certain impact on a radio frequency (RF) receiving coil of the magnetic resonance system. Therefore, the multi-shim coil also has some defects. Compared with the spherical harmonic function shim coil and the multi-shim coil, the local shim coil can simply and efficiently realize magnetic field shimming while reducing the interference to the RF receiving coil. That is, the local shim coil generally may have satisfactory shimming performance. Therefore, in one embodiment, the shim coil disposed in the magnetic resonance system is specifically a local shim coil, that is, the magnetic field distribution model of the shim coil in the embodiments of the present application is specifically the magnetic field distribution model corresponding to the local shim coil, and the shim coil parameters are specifically the parameters corresponding to the local shim coil.

Embodiment 1

FIG. 1 shows a schematic flowchart of a shimming method according to an embodiment of the present application. The shimming method is applied to an electronic device, and the details are as follows.

In S101, the object static magnetic field distribution information corresponding to a target object is acquired, where the object static magnetic field distribution information is the static magnetic field distribution information of the target object under the action of a main magnet of a magnetic resonance system.

The magnetic resonance system is a system capable of realizing magnetic resonance imaging by utilizing the principle of nuclear magnetic resonance. Nuclear magnetic resonance imaging is a process of using radio frequency electromagnetic waves to excite a substance containing atomic nuclei with non-zero spins in a magnetic field to create nuclear magnetic resonance, and then using an induction coil to collect magnetic resonance signals, and processing them mathematically to establish a digital image. The nuclear magnetic resonance system in the embodiments of the present application may include a main magnet for providing a static magnetic field, a gradient coil for providing a gradient magnetic field, and a radio frequency coil for exciting hydrogen atoms and receiving magnetic resonance signals generated by nuclear recovery.

In the embodiments of the present application, the target object is a corresponding tissue or part of the human body or other animal body. Examples include a human brain, a mouse brain, or other tissues or parts. The target object is placed in the magnetic resonance imaging region of the magnetic resonance system. When the main magnet of the magnetic resonance system is in an energized operating state, the instant static magnetic field distribution information of the target object in the magnetic resonance imaging region under the action of the main magnet of the magnetic resonance system is obtained, thus obtaining the object static magnetic field distribution information corresponding to the target object.

In one embodiment, the object static magnetic field distribution information may be a B0 magnetic field image acquired through a two-dimensional multi-echo sequence, that is, a two-dimensional gradient echo (Gradient Recalled Echo, GRE) sequence. The value of each pixel of the B0 magnetic field image represents the magnetic field strength at the corresponding position in the magnetic field. In one embodiment, after the target object is placed in the magnetic resonance imaging region of the magnetic resonance system, and parameters such as the number of echoes, repetition time, and pulse flip angle corresponding to the pulse sequence in the magnetic resonance system are set, the B0 magnetic field imaging is performed on the target object, and the phase map corresponding to each echo is obtained and then unwrapped. Then the least squares method is used to perform linear fitting on the pixels at the same position of every phase map on the echo time. Then the slope value of the fitted straight line is used as the B0 magnetic field value of this position. Then the instant B0 magnetic field image is determined by the obtained B0 magnetic field value at each position in the magnetic resonance imaging region, Exemplarily, the aforementioned number of echoes may be the repetition time of the pulse sequence may be a value between 25 and 300 milliseconds; the five echo times may be set to 3.68 milliseconds, 6.12 milliseconds, 8.56 milliseconds, 11 milliseconds, and 12.44 milliseconds, respectively; and the pulse flip angle may be set to 10 degrees. In one embodiment, since in the magnetic resonance system, the magnetic field strength and the resonance frequency have a fixed corresponding relationship, the above-mentioned B0 magnetic field value can also be expressed by the resonance frequency value which is relatively easy to calculate, apart from the magnetic field strength. Exemplarily, the formula for calculating the magnetic field strength caused by the difference in the magnetic susceptibility of the organism is $$\Delta B_0 = \frac{\Delta \phi}{\gamma \cdot \Delta TE}$$

(where $\Delta B_0$ represents the magnetic field strength caused by the difference in the magnetic susceptibility of the organism, $\Delta \phi$ represents the phase difference of two echoes, $\gamma$ represents the gyromagnetic ratio of the imaged nucleus, $\Delta TE$ represents the time difference between two echoes). The corresponding relationship between the resonance frequency and the magnetic field strength can be expressed by a formula $\Delta \omega_0 = \gamma \cdot \Delta B_0$ (wherein denotes the nuclear magnetic resonance angular frequency). Through these two formulas, the calculation formula of the resonance frequency value can be determined as $$\Delta f = \frac{\Delta \phi}{2\pi \cdot \Delta TE}$$

(where $\Delta f$ represents the shift frequency value caused by the difference in the magnetic susceptibility of the organism). The shift frequency value caused by the difference in the magnetic susceptibility of the organism can be calculated by the calculation formula of the resonance frequency value, so that the B0 magnetic field image caused by the difference in the magnetic susceptibility of the organism is generated based on the shift frequency value.

In S102, the target static magnetic field is determined based on the object static magnetic field distribution information and a preset shim coil magnetic field distribution model.

In the embodiments of the present application, the preset shim coil magnetic field distribution model is a preset magnetic field distribution model corresponding to the shim coil(s) with adjustable parameters. The static magnetic field distribution information of the object obtained in operation S101 is superposed with the shim coil magnetic field distribution model to obtain the target static magnetic field. The target static magnetic field may represent, the static magnetic field of the magnetic resonance system when the magnetic resonance system is in an operating state in which one or more shim coils are superposed and an object to be imaged is present.

In S103, at least one shim coil parameter in the shim coil magnetic field distribution model is adjusted until the magnetic field uniformity of the target static magnetic field satisfies a preset condition, so that at least one target shim coil parameter is then obtained.

After the target static magnetic field is determined, the shim coil parameters in the above-mentioned shim coil magnetic field distribution model can be adjusted according to preset parameter constraints, and the magnetic field uniformity of the target static magnetic field is calculated after each adjustment. When the magnetic field uniformity of the target static magnetic field is adjusted to satisfy the preset condition, the shim coil parameters in the shim magnetic field distribution model at this time are used as the target shim coil parameters. The magnetic field uniformity of the target static magnetic field satisfying the preset condition may be that the standard deviation (also referred to as mean square error) of the magnetic field distribution of the target static magnetic field is less than or equal to a preset threshold. In one embodiment, based on the magnetic field distribution information of the target static magnetic field, the magnetic field strengths at every position of the target static magnetic field can be integrated and then averaged to obtain the average magnetic field strength. Then, based on the difference between the magnetic field strength of each position and the average magnetic field strength, the standard deviation of the magnetic field distribution of the target static magnetic field may be obtained.

In the embodiments of the present application, since the target static magnetic field is determined based on the object static magnetic field distribution information of the target object and the preset shim coil magnetic field distribution model, the target static magnetic field can represent the static magnetic field of the magnetic resonance system when the magnetic resonance system is in the operating state in which the shim coil(s) is superposed and the target object is present is obtained. By adjusting the shim coil parameters until the magnetic field uniformity of the target static magnetic field satisfies the preset condition, the target shim coil parameters that satisfy the shimming effect can be obtained, so that the magnetic resonance system can ensure the uniformity of the static magnetic field distribution during operation based on the target shim coil parameters, thereby improving the magnetic resonance imaging effect.

In some embodiments, the at least one shim coil parameter includes any one or more selected from the group consisting of: a number of channels, a size, a spatial position, a current magnitude, and a number of turns of the at least one shim coil.

In the embodiments of the present application, the shim coil magnetic field distribution model is specifically a magnetic field distribution model corresponding to a local shim coil having multiple channels. The number of channels, coil sizes, spatial positions, current magnitudes, number of turns, etc. in the local shim coil can all be used as adjustable shim coil parameters in the shim coil magnetic field distribution model. By adjusting any one or more of them, the magnetic field distribution uniformity of the target static magnetic field can be adjusted flexibly and accurately, and so the target shim coil parameters that can maximize the magnetic field uniformity of the target static magnetic field can be obtained.

In some embodiments, before acquiring the object static magnetic field distribution information corresponding to the target object, the method further includes:

according to Biot-Savart law, determining the magnetic field distribution information of the shim coil magnetic field distribution model.

In the embodiments of the present application, before acquiring the object static magnetic field distribution information corresponding to the target object, a shim coil magnetic field distribution model in the magnetic resonance system may first be constructed. The shim coil magnetic field distribution model includes adjustable shim coil parameters such as the number of channels, coil sizes, spatial positions, current magnitudes, number of turns, or other shim coil parameters. The magnetic field distribution information corresponding to the shim coil magnetic field distribution model can be obtained according to the Biot-Savart Law. Specifically, electromagnetic field calculation is performed according to Biot-Savart law, so as to determine a shim coil magnetic field distribution model that can represent the magnetic field distribution information of the shim coil(s) in the static magnetic field direction (such as the Z direction) of the main magnet. Exemplarily, the magnetic field distribution information of the shim coil magnetic field distribution model is expressed as follows:

$$b = \frac{\mu_0 I}{4\pi} \int \frac{d\vec{s}' \times (\vec{r} - \vec{r}')}{|\vec{r} - \vec{r}'|^3}$$

where b represents the magnetic field distribution information of the shim coil, I represents the current passing through the shim coil, $\mu_0$ is the vacuum permeability, $d\vec{s}'$ is the small line element of a source current, $\vec{r}$ and $\vec{r}'$ are the field point and the source point, respectively. In this shim coil magnetic field distribution model, the magnitude of $d\vec{s}'$ can be changed by adjusting the coil size parameter; the values of and can be changed by adjusting the spatial position in the shim coil parameters; and the magnitude of I and $d\vec{s}''$ can be changed by adjusting the source current and the number of turns in the shim coil parameters. Therefore, in the shim coil distribution model, when adjusting the shim coil parameters, the magnetic field distribution information of the shim coil magnetic field distribution model can be automatically updated.

In the embodiments of the present application, by accurately determining the shim coil distribution model in advance, the target static magnetic field can subsequently be quickly determined, and the shim performance of the magnetic resonance system can be efficiently and accurately achieved based on the target static magnetic field.

In some embodiments, obtaining the object static magnetic field distribution information corresponding to the target object includes:
obtaining the object static magnetic field distribution information corresponding to each of a number of n target objects, n being a positive integer greater than 1; and accordingly, determining the target static magnetic field based on the object static magnetic field distribution information and the preset shim coil magnetic field distribution model includes:
determining the target static magnetic field based on the respective object static magnetic field distribution information corresponding to each of the n target objects and the preset shim coil magnetic field distribution model.

When the object static magnetic field distribution information corresponding to only one target object is obtained in operation S101, the final determined target shim coil parameters can achieve desired magnetic field uniformity only when the magnetic resonance system tests this target object or an object whose type is consistent with the target object. When testing other objects of different types than the target object, however, the uniformity of the magnetic field during testing cannot be well guaranteed. Therefore, in S101 of this embodiment of the present application, the object static magnetic field distribution information corresponding to each of the target objects may be specifically obtained. Then in operation S103, specifically based on the respective object static magnetic field distribution information corresponding to each of the n target objects, the target static magnetic field including the static magnetic field distribution information of different target objects is determined, so that the target shim coil parameters obtained by adjusting the shim coil parameters based on the magnetic field uniformity of the target static magnetic field can be generally applied to magnetic resonance imaging of various different types of objects, and the universality of the shimming of the magnetic resonance system is improved. In the above, the larger the value of n, the magnetic resonance imaging of more objects the target shim coil parameters determined by the shimming method are applicable to. Exemplarily, n may be equal to five.

In some embodiments, the shim coil magnetic field distribution model includes shim coil units of a number of m channels, m being a positive integer greater than 1. Determining the target static magnetic field based on the respective object static magnetic field distribution information corresponding to each of the n target objects and the preset shim coil magnetic field distribution model may include:
determining the target static magnetic field using the objective function $$F = \sum_{i=1}^{n} \sum_{j=1}^{m} (C_j b_j + B_i)$$

where F denotes the magnetic field distribution information of the target static magnetic field, $C_j$ is the current magnitude of the shim coil unit of the j-th channel in the shim coil magnetic field distribution model, and $b_j$ is the magnetic field distribution information of the shim coil unit of the j-th channel in the shim coil magnetic field distribution model, and $B_i$ is the object static magnetic field distribution information of the i-th target object.

In the shim coil magnetic field distribution model according to the embodiments of the present application, the at least one shim coil includes shim coil units of in channels, where in is a positive integer greater than 1. Exemplarily, as shown in FIG. 2, the shim coil according to the embodiments of the present application may include shim coil units of 5 channels, which are numbered 1 to 5.

Accordingly, in the embodiments of the present application, the magnetic field distribution information of the target static magnetic field may be determined based on the magnetic field distribution information of the in channels of shim coil units in the shim coil magnetic field distribution model and the respective object static magnetic field distribution information of each of the ii target objects. Specifically, the target function can be used to determine the magnetic field distribution information of the target static magnetic field. The objective function may be expressed as follows:

$$F = \sum_{i=1}^{n} \sum_{j=1}^{m} (C_j b_j + B_i)$$

where F represents the magnetic field distribution information of the target static magnetic field; $C_j$ represents the current magnitude of the shim coil unit of the j-th channel in the shim coil magnetic field distribution model, where the value of is specifically related to the number of turns of the shim coil unit and the tiny line elements of the source current and other information; $b_j$ represents the magnetic field distribution information of the shire coil unit of the j-th channel in the shim coil magnetic field distribution model, where the value of $b_j$ can be determined by the expression formula of the magnetic field distribution information determined during the modeling of the shim coil magnetic field distribution model; and $B_i$ represents the object static magnetic field distribution information of the i-th target object.

Through this objective function, the magnetic field distribution of the target static magnetic field can be accurately represented, so that the shim coil parameter adjustment can be accurately realized subsequently according to the objective function, and so the target static magnetic field satisfying the preset condition can be obtained.

In some embodiments, adjusting the shim coil parameters in the shim coil magnetic field distribution model until the magnetic field uniformity of the target static magnetic field satisfies the preset condition to obtain the target shim coil parameters may include:

according to a particle swarm algorithm and the objective function, adjusting the shim coil parameters in the shim coil magnetic field distribution model until a standard deviation of the magnetic field distribution of the target static magnetic field is less than a preset threshold or until the number of iterations of the particle swarm algorithm reaches a preset number, so as to obtain the target shim coil parameters.

In the embodiments of the present application, a certain number of shim coil parameter values may be determined to form a particle swarm according to a constraint range of the shim coil parameters in the shim coil magnetic field distribution model. Thereafter, the following steps are implemented by the particle swarm algorithm:

A1: obtaining an initial set of shim coil parameter values in the particle swarm, and determining the standard deviation of the magnetic field distribution of the target static magnetic field based on the shim coil parameter values and the objective function;

A2: if the standard deviation is less than the preset threshold or the number of iterations of the particle swarm algorithm reaches the preset number, taking the current set of shim coil parameter values as the values of the target shim coil parameters; otherwise, determine the local optimal shim coil parameters and the global optimal shim coil parameters based on the standard deviation;

A3: based on the local optimal shim coil parameters and the global optimal shim coil parameters, obtaining the next set of shim coil parameter values from the particle swarm, and based on the shim coil parameter values and the objective function, determining the standard deviation of the magnetic field distribution of the current target static magnetic field; after that, returning to operation A2.

In the embodiments of the present application, if the standard deviation of the magnetic field distribution of the target static magnetic field is less than the preset threshold, it can directly indicate that the magnetic field distribution of the target static magnetic field is relatively uniform, while the number of iterations of the particle swarm algorithm reaching the preset number can also indicate that currently the relatively optimal target shim coil parameters that can make the magnetic field distribution of the target static magnetic field satisfactorily uniform have been found within the parameter range. Through the particle swarm algorithm, the target shim coil parameters satisfying any one of the above two conditions can be quickly and accurately determined, thereby improving the shimming efficiency.

In some embodiments, adjusting the shim coil parameters in the shim coil magnetic field distribution model according to the particle swarm algorithm and the objective function until the standard deviation of the magnetic field distribution of the target static magnetic field is less than the preset threshold or until the number of iterations of the particle swarm algorithm reaches the preset number so as to obtain the target shim coil parameters may include:

for each shim coil magnetic field distribution model with a different number of channels, adjusting the shim coil parameters in the shim coil magnetic field distribution model according to the particle swarm algorithm and the objective function, until the number of iterations of the particle swarm algorithm reaches the preset number of times to obtain sub-target shim coil parameters corresponding to each of the shim coil magnetic field distribution models;

according to the respective sub-target shim coil parameters corresponding to each of the shim coil magnetic field distribution models and the objective function, determining the standard deviation of the magnetic field distribution of the target static magnetic field corresponding to each of the shim coil magnetic field distribution models;

taking the shim coil magnetic field distribution model with the minimum standard deviation of the magnetic field distribution of the target static magnetic field as the target shim coil magnetic field distribution model, and using the number of channels and the sub-target shim coil parameters of the target shim coil magnetic field distribution model as the target shim coil parameters.

In the shim coil magnetic field distribution model, the number of channels of the shim coil units can be adjusted within a preset range, for example, the range of adjustment of the number of channels can be 3-6: In the embodiments of the present application, the shim coil magnetic field distribution model corresponding to each channel number can be determined by setting the number of channels. For example, four shim coil distribution models with respective channel numbers of 3, 4, 5, and 6 can be determined. After that, in each shim coil magnetic field distribution model corresponding to a fixed number of channels, the shim coil parameters except the number of channels in the shim coil magnetic field distribution model are adjusted according to the particle swarm algorithm and the objective function, until the number of iterations of the particle swarm algorithm reaches the preset number, so as to obtain the optimal shim coil parameters of the shim coil magnetic field distribution model as the sub-target shim coil parameters. Through this method, the stab-target shim coil parameters corresponding to each shim coil magnetic field distribution model corresponding to a fixed number of channels can be determined.

Exemplarily, for a shim coil magnetic field distribution model with a fixed number ml of channels, the size d, spatial position, current magnitude and number of turns of the shim coils in the model can be used as the adjustable shim coil parameters in the shim coil magnetic field distribution model, and accordingly the corresponding particle swarm is designed. Specifically, the particle swarm may include N groups of parameters, the value range of N can be 20-50, and each group of parameters can include a number of D=4*ml shim coil parameter values determined according to the constraint range of the shim coil parameters (specifically including a number of mi size parameter values, a number of ml spatial position parameter values, a number of ml current magnitude parameter values, and a number of ml number of turns parameter values). For the particle swarm, the particle swarm algorithm is implemented through the following operations, to obtain the sub-target shim coil parameters corresponding to the shim coil magnetic field distribution model:

B1: initializing the particle swarm, and assigning a random initial position and velocity to each group of parameters in the particle swarm.

B2: updating the instant particle swarm based on a velocity update formula and a position update formula; where the velocity update formula is as follows:

$$V_i^k = w \cdot V_i^{k-1} + c_1 r_1 (pbest_i - X_i^{k-1}) + c_2 r_2 (gbest_i - X_i^{k-1});$$

The position update formula is:

$$X_i^k = X_i^{k-1} + V_i^{k-1};$$

where in the above formulas, Vik represents the speed of the k-th iteration parameter i, $X_i^k$ represents the position of the k-th iteration parameter i; $pbest_i$ represents the historical optimal position of the parameter i, $gbest_i$ represents the global optimal position of the parameter i; $c_1$, $c_2$ represents the acceleration constants, and may be set to 1.4962; $r_1$, $r_2$ represent two random parameters, ranging from 0 to 1, to increase the randomness of the search; w represents the inertia weight, and may be set to 0.7298, and used to adjust the search range for the solution space. The limit conditions or constraints of the parameters can be set depending on practice. For example, in one embodiment, constraints on the parameters of a. 5-channel local shim coil for mouse brain imaging are given. In the optimization design process, 5 shim coil units are distributed on a cylinder with a diameter of 70 mm ("mm" means millimeter), the number of turns of the coil units is 1, and the current of each coil unit is constrained to [−2 2]A ("A" means unit of current: ampere). The 5 coil units are all identical squares, where the side length is constrained to [20 50] mm, and the angle of the square on the cylinder is constrained to [−π π]. Centered on the center of the mouse brain, the center of the square is constrained to [−25 25] mm on the z-axis.

B3: according to the objective function, calculating the standard deviation of the target static magnetic field obtained after each set of parameters is substituted into the objective function, and determining whether to update the historical optimal position or the global optimal position depending on the standard deviation, Specifically, in the local optimization process, for each group of parameters; the standard deviation value of its current position is compared with the standard deviation value corresponding to its historical optimal position (pbest). If the standard deviation of the current position is less, the historical optimal position is updated with the current position. In the global optimization process, for each set of parameters, the standard deviation value of its current position is compared with the standard deviation value corresponding to its global optimal position (gbest), and if the standard deviation value of the current position is less, the global optimal position is updated with the current position.

B4: determining whether the current number of iterations reaches the preset number, and if the current number of iterations reaches the preset number, using this set of parameters corresponding to the current global optimal position as the sub-target shim coil parameters corresponding to the current shim coil magnetic field distribution model. Otherwise returning to step B2.

In one embodiment, by performing the particle swarm algorithm calculation on the local shim coils of 5 channels through the above operations B1 to B4, the obtained sub-target shim coil parameters include: the currents corresponding to the 5 shim coil units are: 2 A, −1,6256 A, 0,3702 A, −2 A, −1.4978 A, respectively; the side length of each shim coil unit is 20 mm; the angles distributed on the cylinder are 1.0471 radians; 1.9625 radians, −2.9783 radians, 1.5920 radians, and −2.6117 radians, respectively; and the distances from the positions of the coil unit centers on the z-axis to the origin of the coordinate axis are: 15.5 mm, 25.0 mm, −16.9 mm, 5.7 mm, and −7.0 mm, respectively.

Through the above method, after determining the sub-target shim coil parameters of each shim coil magnetic field distribution model having a different number of channels, for each shim coil magnetic field distribution model, the corresponding sub-target shim coil parameters are substituted into the objective function for calculation to determine the standard deviation of the magnetic field distribution of the target static magnetic field corresponding to this shim coil distribution model.

Then, the corresponding shim coil magnetic field distribution model with the minimum standard deviation is determined as the target shim coil magnetic field distribution model with the most uniform magnetic field distribution. At this time, the channel number of the target shim coil distribution model and its corresponding sub-target shim coil parameters are combined as the target shim coil parameters, so as to maximize the shimming effect of the magnetic resonance system.

In the embodiments of the present application, the optimal sub-target shim coil parameters are calculated for each of the shim coil magnetic field distribution models with different channel numbers, then according to the magnetic field distribution uniformity of the target static magnetic field determined by each sub-target shim coil, the target shim coil magnetic field distribution model with the optimal number of channels is determined, so that the channel number of the shim coils can be optimized and the shimming effect can be improved.

In one embodiment, the B0 magnetic field images of 8 objects may be acquired, and the B0 magnetic field images of 5 objects thereof are used as the object static magnetic field distribution information of the target object, and accordingly the target shim coil parameters are obtained through the above operations S101 to S103. Afterwards, the B0 magnetic field images of the remaining three objects are used as a test group, and the static magnetic field shimming effect in the magnetic resonance system is tested based on the target shim coil parameters. In an experiment, after the target shim coil parameters are determined by the method according to the embodiments of the present application, based on the target shim coil parameters, the B0 magnetic field images of three rat brains were used as the test group, and it was found that the non-uniformity of the magnetic field in the magnetic resonance system could be reduced by 75%-37%.

As an example rather than limitation, FIG. 3 shows a comparison of the simulated shimming results of the performance of shim coils with different structures provided by the embodiments of the present application, where MC8 represents a multi-coil with 8 channels, and LC3 represents a multi-coil with 3 channels, and so on; Basic set represents the basic setting, d represents the side length of the coil unit, and L represents the total length of the shim coil. It can be seen from the figure that the local shim coil can achieve a satisfactory shimming effect with a relatively small number of channels. Through the test, the influence of the local shim coil on the signal-to-noise ratio of the RF coil is controlled within 5%, which will not cause great interference to the RF coil while achieving a desired shimming effect.

It should be understood that the order of the sequential numbers assigned to the steps in the above embodiments does not necessarily mean the order of execution, and the execution sequence of the various processes should be determined by its function and internal logic, so that the order of the sequential numbers should not constitute any limitation to the implementation process of the embodiments of the present application.

Embodiment 2

Figure 4:
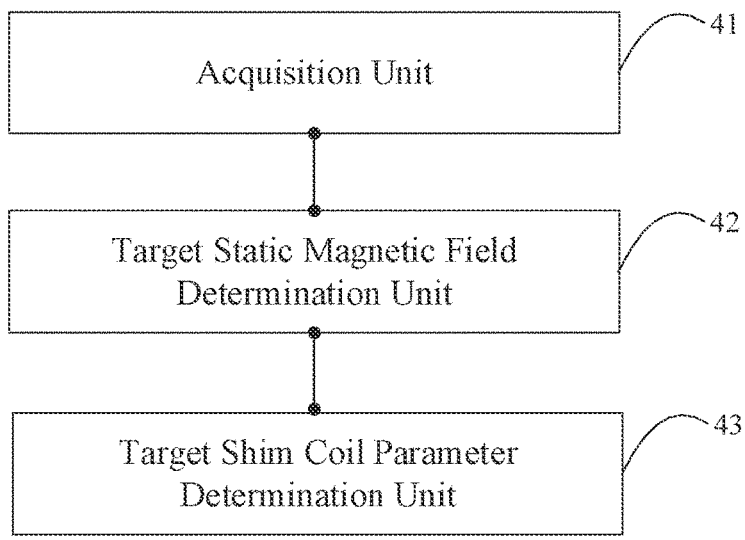
FIG. 4 is a schematic diagram of a shimming device according to an embodiment of the present application.

FIG. 4 shows a schematic diagram of a shimming device provided by an embodiment of the present application. For the convenience of description, only the parts related to the embodiments of the present application are shown.

The shimming device includes an acquisition unit 41, a target static magnetic field determination unit 42, and a target shim coil parameter determination unit 43.

The acquisition unit 41 is configured to obtain object static magnetic field distribution information corresponding to a target object, where the object static magnetic field distribution information is the static magnetic field distribution information of the target object under the action of a main magnet of a magnetic resonance system.

The target static magnetic field determination unit 42 is configured to determine a target static magnetic field based on the object static magnetic field distribution information and a preset shim coil magnetic field distribution model.

The target shim coil parameter determination unit 43 is configured to adjust at least one shim coil parameter in the shim coil magnetic field distribution model until a magnetic field uniformity of the target static magnetic field satisfies a preset condition, so that at least one target shim coil parameter is then obtained.

In some embodiments, the at least one shim coil parameter includes any one or more selected from the group consisting of: a number of channels, a size, a spatial position, a current magnitude, and a number of turns of the at least one shim coil.

In some embodiments, the shimming device further includes:
a model determination unit configured to determine the magnetic field distribution information of the shim coil magnetic field distribution model according to Biot-Savart law.

In some embodiments, the acquisition unit 41 is specifically configured to obtain the object static magnetic field distribution information corresponding to each of a number of n target objects, n being a positive integer greater than 1;
and accordingly, the target static magnetic field determination unit 42 is configured to determine the target static magnetic field based on the respective object static magnetic field distribution information corresponding to each of the n target objects and the preset shim coil magnetic field distribution model.

In some embodiments, the shim coil magnetic field distribution model includes shim coil units of in channels, in being a positive integer greater than 1; the target static magnetic field determination unit 42 is specifically configured to use an objective function $$F = \sum_{i=1}^{n}\sum_{j=1}^{m}(C_j b_j + B_i)$$

to determine the target static magnetic field;
where F denotes the magnetic field distribution information of the target static magnetic field, $C_j$ is the current magnitude of the shim coil unit of the j-th channel in the shim coil magnetic field distribution model, and $b_j$ is the magnetic field distribution information of the shim coil unit of the j-th channel in the shim coil magnetic field distribution model, and $B_i$ is the object static magnetic field distribution information of the i-th target object.

In some embodiment, the target shim coil parameter determination unit 43 is specifically configured to adjust the shim coil parameters in the shim coil magnetic field distribution model according to a particle swarm algorithm and the objective function, until a standard deviation of the magnetic field distribution of the target static magnetic field is less than a preset threshold or until the number of iterations of the particle swarm algorithm reaches a preset number, so as to obtain the target shim coil parameters.

In some embodiments, in the target shim coil parameter determination unit 43, adjusting the shim coil parameters in the shim coil magnetic field distribution model according to the particle swarm algorithm and the objective function until the standard deviation of the magnetic field distribution of the target static magnetic field is less than the preset threshold or until the number of iterations of the particle swarm algorithm reaches the preset number so as to obtain the target shim coil parameters may include:
for each shim coil magnetic field distribution model with a different slumber of channels, adjusting the sub-shim coil parameters in the shim coil magnetic field distribution model according to the particle swarm algorithm and the objective function, until the number of iterations of the particle swarm algorithm reaches the preset number of times to obtain sub-target shim coil parameters corresponding to each of the shim coil magnetic field distribution models;
according to the respective sub-target shim coil parameters corresponding to each of the shim coil magnetic field distribution models and the objective function, determining the standard deviation of the magnetic field distribution of the target static magnetic field corresponding to each of the shim coil magnetic field distribution models; and
taking the shim coil magnetic field distribution model with the minimum standard deviation of the magnetic field distribution of the target static magnetic field as the target shim coil magnetic field distribution model, and using the number of channels and the sub-target shim coil parameters of the target shim coil magnetic field distribution model as the target shim coil parameters.

It should be noted that the information exchange, execution process and other contents between the above-mentioned devices/units are based on the same concept as the method embodiments of the present application. For the specific functions and technical effects, see the method embodiments for details, which will not be repeated here.

Embodiment 3

Figure 5:
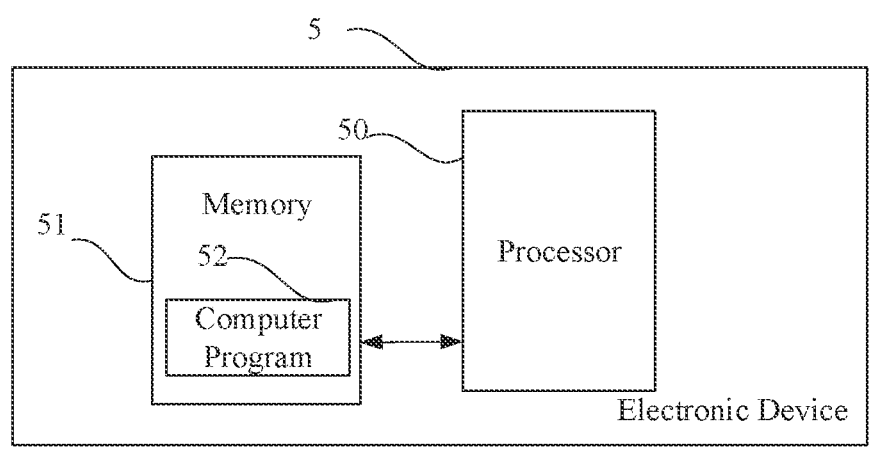
FIG. 5 is a schematic diagram of an electronic device according to an embodiment of the present application.

FIG. 5 is a schematic diagram of an electronic device provided by an embodiment of the present application. As shown in FIG. 5, the electronic device 5 of this embodiment includes a processor 50, a memory 51, and a computer program 52, such as a shim program, stored in the memory 51 and executable by the processor 50. When the processor 50 executes the computer program 52, the operations in each of the foregoing embodiments of the shimming method are performed, for example, operations S101 to S103 shown in FIG. 1. Alternatively or additionally, when the processor 50 executes the computer program 52, the functions of the modules/units in the above device embodiments are implemented, for example, the functions of the acquisition unit 41 through the target shim coil parameter determination unit 43 shown in FIG. 4.

Exemplarily, the computer program 52 may be divided into one or more modules/units, and the one or more modules/units are stored in the memory 51 and executed by the processor 50 to fulfill this application. The one or more modules/units may be a series of computer program instruction segments capable of performing specific functions, and the instruction segments are used to describe the execution process of the computer program 52 in the electronic device 5.

The electronic device 5 may be a computing device such as a desktop computer, a notebook, a palmtop computer, or a cloud server. The electronic device may include, but is not limited to, the processor 50 and the memory 51. Those skilled in the art can understand that FIG. 5 is only an example of the electronic device 5, and does not constitute a limitation to the electronic device 5. It may include more or less components than the one shown, or some components may be combined, or may include some different components, for example, the electronic device may further include an input and output device, a network access device, a bus, or the like.

The so-called processor 50 may be a central processing unit (CPU), or other general-purpose processors, digital signal processors (DSPs), application specific integrated circuits (ASICs), field programmable gate arrays (FPGAs) or other programmable logic devices, discrete gate or transistor logic devices, discrete hardware components, etc. A general purpose processor may be a microprocessor or the processor may be any conventional processor or the like.

The memory 51 may be an internal storage unit of the electronic device 5, such as a hard drive or a memory of the electronic device 5. The memory 51 may also be an external storage device of the electronic device 5, such as a plug-in hard drive, a smart media card (SMC), a secure digital (SD) card, or a flash Card, etc. that is equipped on the electronic device 5. Further, the memory 51 may also include both an internal storage unit and an external storage device. The memory 51 is used to store the computer program and other programs and data required by the electronic device. The memory 51 can also be used to temporarily store data that has been output or will be output.

Those skilled in the art can clearly understand that, for the convenience and brevity of description, the division of the above-mentioned functional units and modules is merely used for illustration. In practical applications, the above-mentioned functions can be allocated to different functional units and modules as required, that is, the internal structure of the device may be divided into different functional units or modules to achieve all or part of the functions described above. The various functional units and modules in the embodiments may be integrated in one processing unit, or each unit may exist physically alone, or two or more units may be integrated into one unit. The above-mentioned integrated units may be implemented in the form of hardware, or may be implemented in the form of software functional units. In addition, the specific names of the functional units and modules are merely for the convenience of distinguishing from one another, and are not used to limit the scope of protection of the present application. For the specific working processes of the units and modules in the above-mentioned system, reference may be made to the corresponding processes in the foregoing method embodiments, which will not be repeated here.

In the foregoing embodiments, the description of each embodiment has its own emphasis. For parts that are not described or not described in detail in a certain embodiment, reference may be made to the relevant descriptions of other embodiments.

Those of ordinary skill in the art will realize that the units and algorithm steps of each example described in conjunction with the embodiments disclosed herein can be implemented in electronic hardware, or a combination of computer software and electronic hardware. Whether these functions are performed in hardware or software depends on the specific application and design constraints of the technical solution. Skilled artisans may implement the described functions using different methods for each particular application, but such implementations should not be considered beyond the scope of this application.

In the embodiments provided in this application, it should be understood that the disclosed apparatuses/electronic devices and methods may be implemented in other forms. For example, the apparatus/electronic device embodiments described above are merely illustrative. For example, the division of the modules or units is only a logical function division. In actual implementation, there can be other division methods. For example, multiple units or components may be combined or may be integrated into another system, or some features may be omitted, or not implemented. On the other hand, the shown or discussed mutual coupling or direct coupling or communication connection may be achieved through the indirect coupling or communication connection between some interfaces, devices or units, and may be in electrical, mechanical or in other forms.

The units described as separate components may or may not be physically separated, and components displayed as units may or may not be physical units, that is, may be located in one place, or may be distributed to multiple network units. Some or all of the units may be selected depending on actual needs to achieve the purposes of the solutions in the embodiments herein.

In addition, the various functional units in the embodiments of the present application may be integrated into one processing unit, or each unit may exist physically alone, or two or more units may be integrated into one unit. The above-mentioned integrated units may be implemented in the form of hardware, or may be implemented in the form of software functional units.

The integrated nodules/units, if implemented in the form of software functional units and sold or used as independent products, may be stored in a computer-readable storage medium, Based on this understanding, the present application can implement all or part of the processes in the methods of the above embodiments, and may also be realized by instructing the relevant hardware through a computer program. The computer program may be stored in a computer-readable storage medium, and when executed by a processor the computer program can perform the operation of the above-mentioned method embodiments. The computer program includes computer program code, which may be in the form of source code, object code, an executable file, or in some intermediate form, or the like. The computer-readable medium may include any entity or device, recording medium, U disk, removable hard disk, magnetic disk, optical disk, computer memory, read-only memory (ROM), Random Access Memory (RAM), electric carrier signal, telecommunication signal, and software distribution medium, etc. that are capable of carrying the computer program code. It should be noted that the contents contained in the computer-readable media may be appropriately increased or decreased according to the requirements of legislation and patent practice in the jurisdiction. For example, in some jurisdictions, the legislation and patent practice provide that computer-readable media do not include electrical carrier signals and telecommunications signals.

The foregoing embodiments are merely used to illustrate the technical solutions of the present application, but not to limit them, Although the present application has been described in detail with reference to the foregoing embodiments, those of ordinary skill in the art should understand that the technical solutions described in the foregoing embodiments can still be modified, or some of the technical features thereof can be equivalently replaced. However, these modifications or substitutions do not make the essence of the corresponding technical solutions deviate from the spirit and scope of the technical solutions of the embodiments of the present disclosure and so should all be included within the scope of protection of this application.

What is claimed is:

1. A shimming method, comprising:
   obtaining object static magnetic field distribution information corresponding to a target object, wherein the object static magnetic field distribution information comprises static magnetic field distribution information of the target object under an action of a main magnet of a magnetic resonance system;
   determining a target static magnetic field based on the object static magnetic field distribution information and a preset shim coil magnetic field distribution model; and
   adjusting at least one shim coil parameter in the preset shim coil magnetic field distribution model until a magnetic field uniformity of the target static magnetic field satisfies a preset condition, and accordingly obtaining at least one target shim coil parameter;
   wherein obtaining the object static magnetic field distribution information corresponding to the target object comprises:
   obtaining object static magnetic field distribution information corresponding to each of a number of n target objects, n being a positive integer greater than 1;
   and wherein accordingly, determining the target static magnetic field based on the object static magnetic field distribution information and the preset shim coil magnetic field distribution model comprises:
   determining the target static magnetic field based on the respective object static magnetic field distribution information corresponding to each of the n target objects and the preset shim coil magnetic field distribution model;
   wherein the adjusting the at least one shim coil parameter in the preset shim coil magnetic field distribution model until the magnetic field uniformity of the target static magnetic field satisfies the preset condition, and accordingly obtaining the at least one target shim coil parameter comprises:
   for each of a plurality of shim coil magnetic field distribution models with different numbers of channels, adjusting at least one sub-shim coil parameter in the preset shim coil magnetic field distribution model according to a particle swarm algorithm and a preset objective function, until the number of iterations of the particle swarm algorithm reaches the preset number of times to obtain at least one sub-target shim coil parameter corresponding to each of the plurality of shim coil magnetic field distribution models;
   determining the standard deviation of the magnetic field distribution of the target static magnetic field corresponding to each of the plurality of shim coil magnetic field distribution models based on the respective at least one sub-target shim coil parameter corresponding to each of the plurality of shim coil magnetic field distribution models and the objective function; and
   taking the preset shim coil magnetic field distribution model with a minimum standard deviation of the magnetic field distribution of the target static magnetic field as a target shim coil magnetic field distribution model, and using the number of channels and the at least one sub-target shim coil parameter of the target shim coil magnetic field distribution model as the at least one target shim coil parameter;
   wherein the for each of a plurality of shim coil magnetic field distribution models with different numbers of channels, adjusting at least one sub-shim coil parameter in the preset shim coil magnetic field distribution model according to a particle swarm algorithm and a preset objective function, until the number of iterations of the particle swarm algorithm reaches the preset number of times to obtain at least one sub-target shim coil parameter corresponding to each of the plurality of shim coil magnetic field distribution models comprises:
   B0, for a shim coil magnetic field distribution model with a fixed number of channels, using a size, a spatial position, a current magnitude, and the number of turns of shim coils in the model as adjustable shim coil parameters in the shim coil magnetic field distribution model, designing a corresponding particle swarm;
   B1: initializing the particle swarm, and assigning a random initial position and velocity to each group of parameters in the particle swarm;
   B2: updating the instant particle swarm based on a velocity update formula and a position update formula; where the velocity update formula is as follows: $V_i^k = w \cdot V_i^{k-1} + c_1 r_1 (\text{pbest}_i - X_i^{k-1}) + c_2 r_2 (\text{gbest}_i - X_i^{k-1})$; the position update formula is: $X_i^k = X_i^{k-1} + V_i^{k-1}$; wherein $V_i^k$ represents a speed of the k-th iteration parameter i, $X_i^k$ represents a position of the k-th iteration parameter i, $\text{pbest}_i$ represents a historical optimal position of the parameter i, $\text{gbest}_i$ represents a global optimal position of the parameter i, c1, c2 represents acceleration constants, r1, r2 represent two random parameters ranging from 0 to 1, w represents an inertia weight;
   B3: according to the preset objective function, calculating a standard deviation of a target static magnetic field obtained after each set of parameters is substituted into the preset objective function, and determining whether to update the historical optimal position or the global optimal position depending on the standard deviation;
   B4: determining whether the current number of iterations reaches the preset number; if yes, using a set of parameters corresponding to the current global optimal position as sub-target shim coil parameters corresponding to the current shim coil magnetic field distribution model; if no, returning to B2.

2. The shimming method as recited in claim 1, wherein the at least one shim coil parameter comprises one or more selected from the group consisting of: a number of channel, a size, a spatial position, a current magnitude, and a number of turns of at least one shim coil.

3. The shimming method as recited in claim 1, further comprising the following operation prior to obtaining the object static magnetic field distribution information corresponding to the target object:
determining magnetic field distribution information of the preset shim coil magnetic field distribution model according to Biot-Savart law.

4. The shimming method as recited in claim 1, wherein the preset shim coil magnetic field distribution model comprises shim coil units of a number of m channels, m being a positive integer greater than 1; wherein determining the target static magnetic field based on the respective object static magnetic field distribution information corresponding to each of the n target objects and the preset shim coil magnetic field distribution model comprises:
determining the target static magnetic field using the preset objective function, wherein the preset objective function is $$F = \sum_{i=1}^{n}\sum_{j=1}^{m}(C_j b_j + B_i);$$

where F represents magnetic field distribution information of the target static magnetic field, $C_j$ represents a current magnitude of a shim coil unit of a j-th channel in the preset shim coil magnetic field distribution model, $b_j$ represents magnetic field distribution information of the shim coil unit of the j-th channel in the preset shim coil magnetic field distribution model, and $B_i$ represents the object static magnetic field distribution information of an i-th target object.

5. An electronic device, comprising a memory, a processor, and a computer program stored in the memory and executable by the processor; wherein when the processor executes the computer program, the electronic device is caused to perform a shimming method comprising the following operations:
obtaining object static magnetic field distribution information corresponding to a target object, wherein the object static magnetic field distribution information comprises static magnetic field distribution information of the target object under an action of a main magnet of a magnetic resonance system;
determining a target static magnetic field based on the object static magnetic field distribution information and a preset shim coil magnetic field distribution model; and
adjusting at least one shim coil parameter in the preset shim coil magnetic field distribution model until a magnetic field uniformity of the target static magnetic field satisfies a preset condition, and accordingly obtaining at least one target shim coil parameter;
wherein obtaining the object static magnetic field distribution information corresponding to the target object comprises:
obtaining object static magnetic field distribution information corresponding to each of a number of n target objects, n being a positive integer greater than 1;
and wherein accordingly, determining the target static magnetic field based on the object static magnetic field distribution information and the preset shim coil magnetic field distribution model comprises:
determining the target static magnetic field based on the respective object static magnetic field distribution information corresponding to each of the n target objects and the preset shim coil magnetic field distribution model;
wherein the adjusting the at least one shim coil parameter in the preset shim coil magnetic field distribution model until the magnetic field uniformity of the target static magnetic field satisfies the preset condition, and accordingly obtaining the at least one target shim coil parameter comprises:
for each of a plurality of shim coil magnetic field distribution models with different numbers of channels, adjusting at least one sub-shim coil parameter in the preset shim coil magnetic field distribution model according to a particle swarm algorithm and a preset objective function, until the number of iterations of the particle swarm algorithm reaches the preset number of times to obtain at least one sub-target shim coil parameter corresponding to each of the plurality of shim coil magnetic field distribution models;
determining the standard deviation of the magnetic field distribution of the target static magnetic field corresponding to each of the plurality of shim coil magnetic field distribution models based on the respective at least one sub-target shim coil parameter corresponding to each of the plurality of shim coil magnetic field distribution models and the objective function; and
taking the preset shim coil magnetic field distribution model with a minimum standard deviation of the magnetic field distribution of the target static magnetic field as a target shim coil magnetic field distribution model, and using the number of channels and the at least one sub-target shim coil parameter of the target shim coil magnetic field distribution model as the at least one target shim coil parameter;
wherein the for each of a plurality of shim coil magnetic field distribution models with different numbers of channels, adjusting at least one sub-shim coil parameter in the preset shim coil magnetic field distribution model according to a particle swarm algorithm and a preset objective function, until the number of iterations of the particle swarm algorithm reaches the preset number of times to obtain at least one sub-target shim coil parameter corresponding to each of the plurality of shim coil magnetic field distribution models comprises:
B0, for a shim coil magnetic field distribution model with a fixed number of channels, using a size, a spatial position, a current magnitude, and the number of turns of shim coils in the model as adjustable shim coil parameters in the shim coil magnetic field distribution model, designing a corresponding particle swarm;
B1: initializing the particle swarm, and assigning a random initial position and velocity to each group of parameters in the particle swarm;
B2: updating the instant particle swarm based on a velocity update formula and a position update formula; where the velocity update formula is as follows: $V_i^k = w \cdot V_i^{k-1} + c_1 r_1 (pbest_i - X_i^{k-1}) + c_2 r_2 (gbest_i - X_i^{k-1})$;
the position update formula is: $X_i^k = X_i^{k-1} + V_i^{k-1}$;
wherein $V_i^k$ represents a speed of the k-th iteration parameter i, $X_i^k$ represents a position of the k-th iteration parameter i, $pbest_i$ represents a historical optimal position of the parameter i, gbest$_i$ represents a global optimal position of the parameter i, c1, c2 represents acceleration constants, r1, r2 represent two random parameters ranging from 0 to 1, w represents an inertia weight;

B3: according to the preset objective function, calculating a standard deviation of a target static magnetic field obtained after each set of parameters is substituted into the preset objective function, and determining whether to update the historical optimal position or the global optimal position depending on the standard deviation;

B4: determining whether the current number of iterations reaches the preset number; if yes, using a set of parameters corresponding to the current global optimal position as sub-target shim coil parameters corresponding to the current shim coil magnetic field distribution model; if no, returning to B2.

6. The electronic device as recited in claim 5, wherein the at least one shim coil parameter comprises one or more selected from the group consisting of: a number of channel, a size, a spatial position, a current magnitude, and a number of turns of at least one shim coil.

7. The electronic device as recited in claim 5, wherein the shimming method further comprises the following operation prior to obtaining the object static magnetic field distribution information corresponding to the target object:
determining magnetic field distribution information of the preset shim coil magnetic field distribution model according to Biot-Savart law.

8. The electronic device as recited in claim 5, wherein the preset shim coil magnetic field distribution model comprises shim coil units of a number of m channels, m being a positive integer greater than 1; wherein determining the target static magnetic field based on the respective object static magnetic field distribution information corresponding to each of the n target objects and the preset shim coil magnetic field distribution model comprises:
determining the target static magnetic field using an the preset objective function, wherein the preset objective function is $$F = \sum_{i=1}^{n}\sum_{j=1}^{m}(C_j b_j + B_i);$$

where F represents magnetic field distribution information of the target static magnetic field, $C_j$ represents a current magnitude of a shim coil unit of a j-th channel in the preset shim coil magnetic field distribution model, $b_j$ represents magnetic field distribution information of the shim coil unit of the j-th channel in the preset shim coil magnetic field distribution model, and $B_i$ represents the object static magnetic field distribution information of an i-th target object.

9. A non-transitory computer-readable storage medium, storing therein a computer program, wherein when the computer program is executed by the processor, the electronic device is caused to perform a shimming method comprising the following operations:
obtaining object static magnetic field distribution information corresponding to a target object, wherein the object static magnetic field distribution information comprises static magnetic field distribution information of the target object under an action of a main magnet of a magnetic resonance system;

determining a target static magnetic field based on the object static magnetic field distribution information and a preset shim coil magnetic field distribution model; and adjusting at least one shim coil parameter in the preset shim coil magnetic field distribution model until a magnetic field uniformity of the target static magnetic field satisfies a preset condition, and accordingly obtaining at least one target shim coil parameter;

wherein obtaining the object static magnetic field distribution information corresponding to the target object comprises:

obtaining object static magnetic field distribution information corresponding to each of a number of n target objects, n being a positive integer greater than 1;

and wherein accordingly, determining the target static magnetic field based on the object static magnetic field distribution information and the preset shim coil magnetic field distribution model comprises:

determining the target static magnetic field based on the respective object static magnetic field distribution information corresponding to each of the n target objects and the preset shim coil magnetic field distribution model;

wherein the adjusting the at least one shim coil parameter in the preset shim coil magnetic field distribution model until the magnetic field uniformity of the target static magnetic field satisfies the preset condition, and accordingly obtaining the at least one target shim coil parameter comprises:

for each of a plurality of shim coil magnetic field distribution models with different numbers of channels, adjusting at least one sub-shim coil parameter in the preset shim coil magnetic field distribution model according to a particle swarm algorithm and a preset objective function, until the number of iterations of the particle swarm algorithm reaches the preset number of times to obtain at least one sub-target shim coil parameter corresponding to each of the plurality of shim coil magnetic field distribution models;

determining the standard deviation of the magnetic field distribution of the target static magnetic field corresponding to each of the plurality of shim coil magnetic field distribution models based on the respective at least one sub-target shim coil parameter corresponding to each of the plurality of shim coil magnetic field distribution models and the objective function; and taking the preset shim coil magnetic field distribution model with a minimum standard deviation of the magnetic field distribution of the target static magnetic field as a target shim coil magnetic field distribution model, and using the number of channels and the at least one sub-target shim coil parameter of the target shim coil magnetic field distribution model as the at least one target shim coil parameter;

wherein the for each of a plurality of shim coil magnetic field distribution models with different numbers of channels, adjusting at least one sub-shim coil parameter in the preset shim coil magnetic field distribution model according to a particle swarm algorithm and a preset objective function, until the number of iterations of the particle swarm algorithm reaches the preset number of times to obtain at least one sub-target shim coil parameter corresponding to each of the plurality of shim coil magnetic field distribution models comprises:

B0, for a shim coil magnetic field distribution model with a fixed number of channels, using a size, a spatial position, a current magnitude, and the number of turns of shim coils in the model as adjustable shim coil parameters in the shim coil magnetic field distribution model, designing a corresponding particle swarm;

B1: initializing the particle swarm, and assigning a random initial position and velocity to each group of parameters in the particle swarm;

B2: updating the instant particle swarm based on a velocity update formula and a position update formula; where the velocity update formula is as follows: $V_i^k = w \cdot V_i^{k-1} + c_1 r_1 (pbest_i - X_i^{k-1}) + c_2 r_2 (gbest_i - X_i^{k-1})$; the position update formula is: $X_i^k = X_i^{k-1} + V_i^{k-1}$; wherein $V_i^k$ wherein Vik represents a speed of the k-th iteration parameter i, $X_i^k$ represents a position of the k-th iteration parameter i, $pbest_i$ represents a historical optimal position of the parameter i, $gbest_i$ represents a global optimal position of the parameter i, c1, c2 represents acceleration constants, r1, r2 represent two random parameters ranging from 0 to 1, w represents an inertia weight;

B3: according to the preset objective function, calculating a standard deviation of a target static magnetic field obtained after each set of parameters is substituted into the preset objective function, and determining whether to update the historical optimal position or the global optimal position depending on the standard deviation;

B4: determining whether the current number of iterations reaches the preset number; if yes, using a set of parameters corresponding to the current global optimal position as sub-target shim coil parameters corresponding to the current shim coil magnetic field distribution model; if no, returning to B2.

10. The non-transitory computer-readable storage medium as recited in claim 9, wherein the at least one shim coil parameter comprises one or more selected from the group consisting of: a number of channel, a size, a spatial position, a current magnitude, and a number of turns of at least one shim coil.

11. The non-transitory computer-readable storage medium as recited in claim 9, wherein the shimming method further comprises the following operation prior to obtaining the object static magnetic field distribution information corresponding to the target object:

determining magnetic field distribution information of the preset shim coil magnetic field distribution model according to Biot-Savart law.

12. The non-transitory computer-readable storage medium as recited in claim 9, wherein the preset shim coil magnetic field distribution model comprises shim coil units of a number of m channels, m being a positive integer greater than 1; wherein determining the target static magnetic field based on the respective object static magnetic field distribution information corresponding to each of the n target objects and the preset shim coil magnetic field distribution model comprises:

determining the target static magnetic field using an the preset objective function, wherein the preset objective function is $$F = \sum_{i=1}^{n} \sum_{j=1}^{m} (C_j b_j + B_i);$$

where F represents magnetic field distribution information of the target static magnetic field, $C_j$ represents a current magnitude of a shim coil unit of a j-th channel in the preset shim coil magnetic field distribution model, $b_j$ represents magnetic field distribution information of the shim coil unit of the j-th channel in the preset shim coil magnetic field distribution model, and $B_i$ represents the object static magnetic field distribution information of an i-th target object.

* * * * *